United States Patent
Takenouchi et al.

[11] Patent Number: 6,040,158
[45] Date of Patent: Mar. 21, 2000

[54] PROCESS FOR PREPARING SUGAR NUCLEOTIDE

[75] Inventors: Kenji Takenouchi; Tomoki Hamamoto; Toshitada Noguchi, all of Choshi, Japan

[73] Assignee: Yamasa Corporation, Chiba, Japan

[21] Appl. No.: 09/068,198

[22] PCT Filed: Aug. 29, 1997

[86] PCT No.: PCT/JP97/03021

§ 371 Date: May 5, 1998

§ 102(e) Date: May 5, 1998

[87] PCT Pub. No.: WO98/11248

PCT Pub. Date: Mar. 19, 1998

[30] Foreign Application Priority Data

Sep. 11, 1996 [JP] Japan .................................... 8-262470
Oct. 7, 1996 [JP] Japan .................................... 8-284723
Jan. 23, 1997 [JP] Japan .................................... 9-024348

[51] Int. Cl.$^7$ ............................ C12P 19/30; C12P 19/40; C12P 19/32; C12P 19/26; C12P 19/00
[52] U.S. Cl. ................................ 435/89; 435/88; 435/92; 435/85; 435/84; 435/255.1; 435/171
[58] Field of Search ................. 435/89, 85, 84, 435/72, 255.1, 171, 88, 92

[56] References Cited

U.S. PATENT DOCUMENTS 2,844,514 7/1958 Morell et al. ............................... 435/89
3,138,539 6/1964 Laufer et al. ............................... 435/89

FOREIGN PATENT DOCUMENTS 1-500560 3/1989 Japan .
7-500248 1/1995 Japan .

OTHER PUBLICATIONS

Enzyme Nomenclature, Academic Press, New York, pp. 254–260, 1984.
Kalckar, Biochim. Biophys. Acta 12: 250–264 (1953).
Chemical Abstracts 84(7): 41909f (1976).
Chemical Abstracts 72(7): 41686h (1970).
Chemical Abstracts 69(25): 10397Sa (1968).
Kawaguchi et al, Agr. Biol. Chem. 34(6): 908–918 (1970).
Kimura et al, J. Bacteriol. 125(2): 744–746 (1976).
Heidlas et al, J. Org. Chem 57(1): 152–157 (1992).

*Primary Examiner*—Francisco Prats
*Attorney, Agent, or Firm*—Wenderoth, Lind & Ponack L.L.P.

[57] ABSTRACT

A process for preparing a sugar nucleotide from a nucleotide by using a yeast cell, characterized in that both a nucleoside diphosphate-sugar pyrophosphorylase and a sugar 1-phosphate are present in the reaction system. According to this process, various sugar nucleotides, which have been prepared only in low productivity by the conventional yeast cell process, can be efficiently prepared.

18 Claims, 2 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 29 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:1:

GCGAATTCTG ATATACTGGG ATGCGATAC                                29

(2) INFORMATION FOR SEQ ID NO:2:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:2:

ACGTCGACAC CGATACGGAT GTATCTT                                  27

(2) INFORMATION FOR SEQ ID NO:3:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:3:

TAGAATTCAA CTCCTCCCTG CCTAATCCCC C                             31

(2) INFORMATION FOR SEQ ID NO:4:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:4:

TTGGATCCCG GCATTATCCA GACGTTTGCT T                             31

(2) INFORMATION FOR SEQ ID NO:5:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:5:

```
ATGCCGAATT CCCGTCGAAA CTGA                                              24

(2) INFORMATION FOR SEQ ID NO:6:

(i) SEQUENCE CHARACTERISTICS:
        (A) LENGTH:  24 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION: SEQ ID NO:6:

GGAATTCCGT TGGGGAAATT GCCG                                              24
```

PROCESS FOR PREPARING SUGAR NUCLEOTIDE

BACKGROUND OF THE INVENTION

1. Field of the Invention

The present invention relates to a process for preparing sugar nucleotides, which are important substrates in the synthesis of oligosaccharides.

2. Description of the Related Art

Recent remarkable progress in sugar-chain science has clarified some of sugar's physiological roles, which makes it possible to develop pharmaceuticals and functional materials based on oligosaccharides possessing physiological activities. However, only limited types of oligosaccharides are currently available on the market, and in addition, they are extremely expensive. Moreover, these oligosaccharides can be produced only on a reagent level, and a mass-production method for them has not yet been fully established.

Conventionally, oligosaccharides have been produced by way of extraction from natural substances, chemical synthesis, enzymatic synthesis, or a combination of these. Among these processes, enzymatic synthesis has been considered best suited for mass-production for the following reasons: (1) enzymatic synthesis does not require intricate procedures, such as protection and removal of protection, which are required for chemical synthesis; (2) substrate specificities of enzymes enable the synthesis of oligosaccharides having highly structural specificities. In addition, recent progress in recombinant DNA technology have made it possible to mass-produce various types of enzymes economically and in large quantities, also contributing to establishing the superiority of enzymatic synthesis over other processes.

Two processes for the synthesis of oligosaccharides by use of enzymatic synthesis are available: a process that makes use of the reverse reaction of a hydrolase, and a process that makes use of a glycosyltransferase. The former has an advantage that it can employ inexpensive monosaccharides as the substrate, but, because it employs the reverse reaction to the hydrolysis reaction, it is not necessarily the best process for the synthesis of oligosaccharides in terms of yield and application to oligosaccharides possessing a complicated structure.

In contrast, the latter makes use of a glycosyltransferase and has an advantage over the former in terms of the yield and application to the synthesis of oligosaccharides possessing a complicated structure. Moreover, the mass-production of various types of glycosyltransferase enabled by recent progress in recombinant DNA technology also contributes to realization of this process.

However, sugar nucleotides, which are sugar donors used in a synthesis that makes use of a glycosyltransferase, are with few exceptions still expensive, and are provided only in small amounts on reagent levels. For example, there have been reported processes for preparing uridine diphosphate-N-glucose (UDPG), which is a donor of glucose contained in core parts of a variety of physiologically active sugar-chains, and the processes include a chemical synthesis method making use of uridylic acid (UMP) and glucose 1-phosphate (G-1-P), and a yeast cell method making use of UMP and glucose as the substrates (T. Tochikura et al., J. Ferment. Technol., 46, 957 (1968), S. Shirota, et al., Agric. Biol. Chem., 35, 325 (1971), and S. Watanabe and I Takeda, and Agric. Biol. Chem., 36, 2265 (1972)), but problems still remain to be solved before industrial production is realized.

The inventors of the present invention have carried out studies on a process for preparing UDPG by conventional yeast cell methods, in which only a small amount of UDPG was produced and 60% or more of the added UMP was converted to uridine triphosphate (UTP) or uridine diphosphate (UDP). Therefore, these methods have no value as a process for the synthesis of UDPG in the actual production.

Accordingly, the present invention is directed to providing a process for preparing sugar nucleotides such as UDPG by improving conventional yeast cell methods.

SUMMARY OF THE INVENTION

The inventors of the present invention have carried out studies to achieve the aforementioned objectives, and found that for the synthesis of UDPG through use of yeast it is important that there be coupled three systems of reaction; a first system in which UTP is synthesized from UMP, a second system in which G-1-P is synthesized from glucose, and a third system in which UDPG is synthesized from UTP and G-1-P; and that a reaction in which UTP is synthesized from UMP occurs relatively smoothly, whereas activity for synthesizing G-1-P and activity for synthesizing UDPG from UTP and G-1-P are weak and not effectively coupled, to thereby reduce production of target UDPG.

In view of the foregoing, the present inventors have conducted further studies and found that, when yeast is used, synthesis of UTP instead of UDPG should be the aim, and that allowing UDP-glucose pyrophosphorylase and G-1-P to coexist in the reaction system enables each of the enzymatic reactions to be effectively coupled, to thereby achieve a high production yield of the intended UDPG. Moreover, this approach has been confirmed to be applicable to the synthesis of not only UDPG but also other sugar nucleotides. The present invention was accomplished based on these findings.

Accordingly, the present invention provides a process for preparing a sugar nucleotide from a nucleotide by use of yeast cells, characterized in that both a nucleoside diphosphate-sugar pyrophosphorylase and a sugar 1-phosphate are present in the reaction system.

DESCRIPTION OF THE PREFERRED EMBODIMENT

Figure 1:
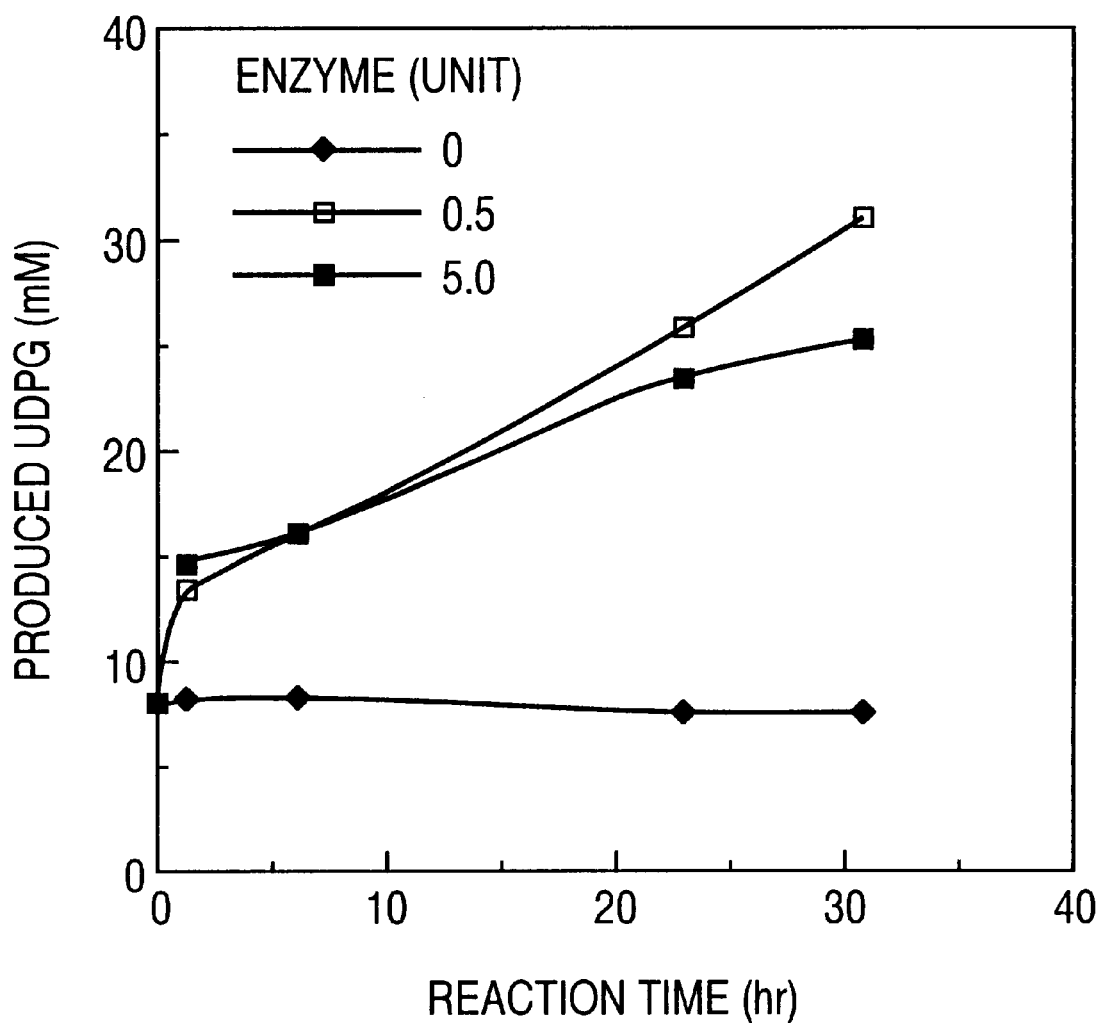
FIG. 1 shows chronological changes in the production yield of UDPG.

The sugar nucleotides used in the present invention are not particularly limited so long as they are known sugar nucleotides. Specific examples include UDP-sugars such as UDPG, UDP-galactose, and UDP-glucuronic acid; GDP-sugars such as GDP-mannose, GDP-fucose, and GDP-glucose; ADP-sugars such as ADP-glucose; dTDP-sugars such as dTDP-glucose and dTDP-galactose; and CDP-sugars such as CDP-glucose.

A variety of types of yeast may be used in the reactions without any particular limitation so long as they have hitherto been employed in conventional processes for the production of nucleotides, sugar nucleotides, and the like. Specifically, there may be used different types of yeast such as those which belong to the genus Zygosaccharomyces, the genus Saccharomyces, the genus Candida, the genus Torulopsis, the genus Hansenula, the genus Debaryomyces, etc. Although viable or dry yeast may be used, dry yeast is preferred from the point of reaction yield.

The nucleoside diphosphate-sugar pyrophosphorylases which are caused to coexist in the reaction system are not particularly limited to those derived from a specific type, and those derived from animals, plants, and microorganisms may be used. However, nucleoside diphosphate-sugar pyrophosphorylases derived from microorganisms are preferred from the point of convenience in preparation of enzymes. When the nucleoside diphosphate-sugar pyrophosphorylase used in the process has been cloned, a gene of the cloned nucleoside diphosphate-sugar pyrophosphorylase may be used to mass-produce the enzyme through a customary method using *Escherichia coli* and the like as the host, to thereby prepare the enzyme.

Such nucleoside diphosphate-sugar pyrophosphorylases may take any form so long as they exhibit the activity. Specific examples include cells of a microorganism, treated cell products, and enzymatic preparations obtained from the treated cell products.

Microorganism cells are cultivated in a culture medium which enables the cells to grow in a customary method, and are then subjected to centrifugation, to thereby collect the cells. The following is a specific example of preparing microorganism cells by use of cells belonging to the genus Bacillus or *Escherichia coli*: Examples of a culture medium include bouillon culture medium, LB culture medium (1% tryptone; 0.5% yeast extract; 1% common salt), and 2×YT culture medium (1.6% tryptone; 1% yeast extract; 0.5% common salt). The cells are inoculated to an appropriate medium and incubated at about 30–50° C. for about 10–50 hours with stirring as needed. The thus-obtained culture solution is subjected to centrifugal separation to collect microorganism cells, to thereby prepare microorganism cells having nucleoside diphosphate-sugar pyrophosphorylase activity.

Examples of treated cell products include destructed cell products as well as modified products of cell walls or plasma membranes of the cells obtained from the microorganism cells described above through customary means such as mechanical destruction (by use of a Waring blender, French press, homogenizer, mortar, or the like), freezing and thawing, self digestion, drying (e.g. freeze drying, air drying), enzymatic treatment (by use of lysozyme, or the like), ultrasonic treatment, or chemical treatment (e.g. acid or alkali treatment).

Examples of enzymatic preparations include crude or purified enzymes obtained from the treated cell products described above by subjecting fractions having nucleoside diphosphate-sugar pyrophosphorylase activity to a customary process for purified enzymes, such as salting-out, isoelectric precipitation, organic solvent precipitation, dialysis, or any of a variety of chromatography techniques.

The sugar 1-phosphates and nucleotides (nucleoside monophosphates) which are added to the reaction mixture may be suitably selected in accordance with the type of the target sugar nucleotide. They may be available on the market or prepared according to a known method. The concentration of respective materials preferably falls within the range of about 1 to about 200 mM, more preferably about 10 to about 100 mM.

Specific examples of combinations of nucleoside diphosphate-sugar pyrophosphorylases, nucleotides, and sugar 1-phosphates which are used in the synthesis of sugar nucleotides are shown in Table 1 below.

TABLE 1

| Sugar nucleotide | Nucleotide | Sugar 1-phosphate | Nucleoside diphosphate sugar pyrophosphorylase |
|---|---|---|---|
| (1) UDP-sugar | | | |
| UDP-glucose | UMP | glucose 1-phosphate | UDP-glucose pyrophosphorylase (E.C. 2.7.7.9) |
| UDP-galactose | UMP | galactose 1-phosphate | UDP-galactose pyrophosphorylase (E.C. 2.7.7.10) |
| UDP-glucuronic acid | UMP | glucuronate 1-phosphate | UDP-glucuronate pyrophosphorylase (E.C. 2.7.7.44) |
| (2) GDP-sugar | | | |
| GDP-mannose | GMP | mannose 1-phosphate | GDP-mannose pyrophosphorylase (E.C. 2.7.7.13) |
| GDP-fucose | GMP | fucose 1-phosphate | GDP-fucose pyrophosphorylase (E.C. 2.7.7.30) |
| GDP-glucose | GMP | glucose 1-phosphate | GDP-glucose pyrophosphorylase (E.C. 2.7.7.34) |
| (3) ADP-sugar | | | |
| ADP-glucose | AMP | glucose 1-phosphate | ADP-glucose pyrophosphorylase (E.C. 2.7.7.27) |
| (4) dTDP-sugar | | | |
| dTDP-glucose | dAMP | glucose 1-phosphate | dTDP-glucose pyrophosphorylase (E.C. 2.7.7.24) |
| dTDP-galactose | dAMP | galactose 1-phosphate | dTDP galactose pyrophosphorylase (E.C. 2.7.7.32) |
| (5) CDP-sugar | | | |
| CDP-glucose | CMP | glucose 1-phosphate | CDP glucose pyrophosphorylase (E.C. 2.7.7.33) |

In place of the aforementioned sugar 1-phosphates, a production system for sugar 1-phosphate may be present in the reaction mixture. Examples include a G-1-P production system making use of a combination of saccharose and saccharose phosphorylase (E. J. Vandamme et al., Adv. Appl. Microbiol., 32, 163–201 (1987)), and another G-1-P production system making use of a combination of glycogen and glycogen phosphorylase (P. H. Strausbauch et al., Methods in Enzymology, 11, 671–675).

In addition to the above-described enzymes and substrates, an inorganic phosphoric acid and energy sources are preferably added to the reaction system.

Useful inorganic phosphoric acids include phosphates such as potassium phosphate, which may be used either as is or, preferably, in the form of a phosphate buffer. The concentration of the inorganic phosphoric acid during use preferably falls within the range of about 10 to about 500 mM, and more preferably about 100 to about 300 mM. Also, the pH of the phosphate buffer may be suitably determined within the range of about 6.0 to about 9.0.

Examples of available energy sources include sugars such as glucose, fructose, and sucrose; and organic acids such as acetic acid and citric acid.

The synthetic reactions of sugar nucleotides comprise the following steps. Yeast cells, nucleotide, sugar 1-phosphate, and a saccharide or organic acid serving as an energy source are added to a phosphate buffer. Nucleoside diphosphate-sugar pyrophosphorylase is also added in an amount of about 0.001 unit/ml or more, preferably in an amount of about 0.01 to 100 unit/ml, and subsequently the mixture is allowed to react at a temperature of not higher than approximately 30° C., preferably at about 5° C. to about 20° C., for about 1 hour to about 50 hours with stirring as needed.

Sugar 1-phosphates and nucleoside diphosphate-sugar pyrophosphorylase may be added either when the reaction is started or, preferably, when the production of a nucleoside triphosphate corresponding to the added nucleotide is maximized, after the reaction mixture is subjected to treatment such as heat treatment at a temperature of not lower than approximately 60° C. for about 5 minutes or longer, which deactivates enzymes derived from yeast to thereby allow the enzymatic reaction to continue.

The thus-obtained sugar nucleotides may be isolated and purified by customary isolation and purification methods (ion exchange chromatography, adsorption chromatography, salting out, etc.) employed for sugar nucleotides.

EXAMPLES

The present invention will next be described in detail by way of examples, which should not be construed as limiting the invention. In the examples, all procedures, including preparation of DNA, cleavage with restriction enzymes, ligation of DNA by T4 DNA ligase, and transformation of *Escherichia coli* were performed in accordance with "Molecular Cloning" (edited by Maniatis et al., Cold Spring Harbor Laboratory, Cold Spring Harbor, N.Y. (1982)). Restriction enzymes, AmpliTaq DNA polymerase, and T4 DNA ligase were obtained from Takara Shuzo Co., Ltd. Furthermore, sugar nucleotides contained in the reaction mixture were determined by HPLC. Specifically, there was employed a system wherein an ODS-AQ 312 column made by YMC was used for separation and 0.5 M potassium dihydrogenphosphate solution was used as an eluent, or alternatively, a system wherein an ODS-AM 303 column made by YMC was used for separation and 0.2 M triethylamine-acetic acid (pH 8.0) was used as an eluent.

Example 1

Synthesis (1) of UDPG (1) Cloning of a Gene of *Escherichia coil* UDP-glucose Pyrophosphorylase Chromosomal DNA of *Escherichia coli* K12 strain JM109 (obtained from Takara Shuzo Co., Ltd.) was prepared by the method of Saito and Miura (Biochim. Biophys. Acta., 72, 619 (1963)). By use of the obtained chromosomal DNA as a template, the following two primer DNAs were synthesized in accordance with a customary method. The *Escherichia coli* UDP-glucose pyrophosphorylase (galU) gene (Weissborn et al., J. Bacteriol., 176, 2611 (1994)) was amplified by PCR.

Primer (A): 5'-GCGAATTCTGATATACTGGGATGCG
ATAC-3' (SEQ ID NO:1)

Primer (B): 5'-ACGTCGACACCGATACGGATGTATCT
T-3' (SEQ ID NO:2)

PCR amplification of the galU gene was performed by use of a DNA Thermal Cycler (Perkin-Elmer Cetus Instrument Co.) through 25 cycles of treatment, each cycle consisting of the steps of thermal denaturation (94° C., 1 minute), annealing (55° C., C., 1.5 minutes), and polymerization (72° C., 1.5 minutes), of a reaction mixture (100 µl) containing 50 mM potassium chloride, 10 mM Tris-hydrochloric acid (pH 8.3), 1.5 mM magnesium chloride, 0.001% gelatin, template DNA (0.1 µg), primer DNAs (A) and (B) (0.2 µM respectively), and AmpliTaq DNA polymerase (2.5 units).

After amplification of the gene, the reaction mixture was treated with a phenol/chloroform (1:1) mixture, and to an aqueous fraction was added ethanol in an amount twice the volume of the aqueous fraction to thereby precipitate DNA. The collected DNA precipitates were separated by agarose gel electrophoresis in accordance with the method of the literature ("Molecular Cloning," referred to above) to purify DNA fragments of 1.0 kb. The DNA was cleaved with restriction enzymes EcoRI and SalI and ligated with plasmid pTrc99A (obtained from Pharmacia Biotech. Co.) which had been digested with the same restriction enzymes EcoRI and SalI, using a T4 DNA ligase. The *Escherichia coli* K12 strain JM109 was transformed with the ligation mixture, and plasmid pTrc-galU was isolated from the obtained ampicillin-resistant transformant. The pTrc-galU is a product obtained by inserting into pTrc99A, at the EcoRI-SalI cleavage sites downstream of the trc promoter, an EcoRI-SalI DNA fragment containing the *Escherichia coli* galU gene.

(2) Preparation of *Escherichia coli* UDP-glucose Pyrophosphorylase

*Escherichia coli* JM109 harboring plasmid pTrc-galU was inoculated to a 2×YT culture medium (300 ml) containing 100 mg/l of ampicillin and was then subjected to shaking culture at 37° C. When the culture reached $4 \times 10^8$ cells/ml, IPTG was added to the culture so that the final concentration thereof became 1 mM, and shaking culture was further carried out for 2.5 hours at 37° C. The cells were suspended in a buffer (60 ml) containing 50 mM Tris-hydrochloric acid (pH 7.5), 5 mM EDTA, 0.1% Triton X-100, and 0.2 mg/ml lysozyme. The cell suspension was maintained at 37° C. for one hour and then subjected to ultrasonic treatment so as to destroy the cells. The cellular residue was removed through additional centrifugation (20,000×g, 10 minutes). The thus-obtained supernatant fraction was provided as an enzyme sample. The UDP-glucose pyrophosphorylase activity of the enzyme sample and that of the reference bacterium (*Escherichia coli* JM109 harboring pTrc99A) are shown in Table 2 below.

TABLE 2

| Strain | UDP-glucose pyrophosphorylase activity (units/mg-protein) |
| --- | --- |
| JM109/pTrc99A | <0.5 |
| JM109/pTrc-galU | 20.4 |

The unit UDP-glucose pyrophosphorylase activity was determined through measurement and calculation by use of the following method.

An enzyme sample was added to 50 mM Tris-hydrochloric acid buffer (pH 8.0) containing 5 mM magnesium chloride, 6 mM UTP, and 6 mM G-1-P, and the mixture was incubated at 37° C. to undergo reaction. The enzyme was inactivated by thermal treatment at 100° C. for five minutes. UDPG in the reaction mixture was determined by HPLC and the activity corresponding to formation of 1 µmol of UDPG at 37° C. for one minute is defined as one unit.

(3) Preparation of a UDPG-UTP Solution by Use of Dry Baker's Yeast

A reaction mixture (20 ml) of 40 mM UMP, 100 mM glucose, 200 mM sodium phosphate (pH 8.0), and 10 mM magnesium chloride was placed in a 100-ml beaker. Dry baker's yeast (2 g, Oriental Yeast Industries K. K.) was suspended in the reaction mixture. The mixture was allowed to react at 20° C. for nine hours with stirring. After completion of the reaction, the reaction mixture was treated at 100° C. for five minutes and the yeast cells were removed from the reaction mixture by centrifugation (2,000×g, 10 minutes). When the recovered supernatant was subjected to HPLC analysis, a yield of 7.9 mM UDPG and 21.9 mM UTP was confirmed.

(4) Synthesis of UDPG by Addition of UDPG Pyrophosphorylase and G-1-P to the UDPG-UTP Solution To the above-described UDPG-UTP solution (100 ml) was added G-1-P so that the final concentration thereof became 30 mM, and the enzyme sample as described in Example 2 was added so that the concentration of UDP-glucose pyrophosphorylase became 0.5 units/ml. The mixture was allowed to react at 30° C. for 30 hours. When the reaction mixture was subjected to HPLC analysis, a yield of 30.9 mM UDPG was confirmed.

Example 2

Synthesis (2) of UDPG

The procedures of (3) and (4) of Example 1 were performed by addition of UDP-glucose pyrophosphorylase in an amount (as enzyme unit) of 0 unit, 0.5 units, or 5 units, to thereby obtain UDPG.

Chronological changes in the amount of formation of UDPG are shown in FIG. 1.

Example 3

Synthesis (3) of UDPG (1) Cloning of a Gene of *Escherichia coil* Maltdextrin Phosphorylase Chromosomal DNA of *Escherichia coil* K12 strain JM109 (obtained from Takara Shuzo Co., Ltd.) was prepared by the method of Saito and Miura (Biochim. Biophys. Acta., 72, 619 (1963)). By use of the obtained chromosomal DNA as a template, the following two primer DNAs were synthesized in accordance with a customary method. The *Escherichia coli* maltdextrin phosphorylase (maip) gene (Nature, 313(6002), 500–502 (1985)) was amplified by PCR.

Primer (C): 5'-TAGAATTCAACTCCTCCCTGCCT
AATCCCCC-3'  (SEQ ID NO:3)

Primer (D): 5'-TTGGATCCCGGCATTATCCAGAC
GTTTGCTT-3'  (SEQ ID NO:4)

PCR amplification of the malp gene was performed by use of a DNA Thermal Cycler (Perkin-Elmer Cetus Instrument Co.) through 25 cycles of treatment, each cycle consisting of the steps of thermal denaturation (94° C., 1 minute), annealing (60° C., 1.5 minutes), and polymerization (72° C., 3 minutes), of a reaction mixture (100 μl) containing 50 mM potassium chloride, 10 mM Tris-hydrochloric acid (pH 8.3), 1.5 mM magnesium chloride, 0.001% gelatin, template DNA (0.1 μg), primer DNAs (C) and (D) (0.2 μM respectively), and AmpliTaq DNA polymerase (2.5 units).

After amplification of the gene, the reaction mixture was treated with a phenol/chloroform (1:1) mixture, and to an aqueous fraction was added ethanol in an amount twice the volume of the aqueous fraction to thereby precipitate DNA. The collected DNA precipitates were separated by agarose gel electrophoresis in accordance with the method of the literature ("Molecular Cloning," referred to above) to purify DNA fragments of 2.0 kb. The DNA was cleaved with restriction enzymes EcoRI and BamHI and ligated with plasmid pTrc99A (obtained from Pharmacia Biotech. Co.) which had been digested with the same restriction enzymes EcoRI and BamHI using a T4 DNA ligase. The *Escherichia coli* K12 strain JM109 was transformed by use of the ligation mixture, and plasmid pTrc-malP was isolated from the obtained ampicillin-resistant transformant. The pTrc-malP is a product obtained by inserting into pTrc99A, at the EcoRI-BamHI cleavage sites downstream of the trc promoter, an EcoRI-BamHI DNA fragment containing the promoter and structural gene of *Escherichia coli* malp.

(2) Preparation of *Escherichia coli* Maltdextrin Phosphorylase *Escherichia coli* JM109 harboring plasmid pTrc-malP was inoculated to a 2×YT culture medium (300 ml) containing 100 mg/l of ampicillin and was then subjected to shaking culture at 37° C. for eight hours. When the culture reached 4×10⁸ cells/ml, IPTG was added to the culture so that the final concentration thereof became 1 mM, and shaking culture was further carried out for five hours at 37° C.

After cultivation, the cells were collected by centrifugation (9,000×g, 10 minutes) and then suspended in a buffer (60 ml) containing 50 mM Tris-hydrochloric acid (pH 7.5), 5 mM EDTA, 0.1% Triton X-100, and 0.2 mg/ml lysozyme. The suspension was maintained at 37° C. for one hour and then subjected to ultrasonic treatment so as to destroy the cells. The cellular residue was removed by additional centrifugation (9,000×g, 10 minutes). The thus-obtained supernatant fraction was provided as an enzyme sample. The maltdextrin phosphorylase activity of the enzyme sample and that of the reference bacterium (*Escherichia coli* JM109 harboring pTrc99A) are shown in Table 3 below.

TABLE 3

| Strain | Maltdextrin phosphorylase activity (units/mg-protein) |
| --- | --- |
| JM109/pTrc99A | 1.5 |
| JM109/pTrc-malP | 93.8 |

The unit maltdextrin phosphorylase activity was determined through measurement and calculation by use of the following method. A maltdextrin phosphorylase enzyme sample was added to 50 mM potassium phosphate buffer (pH 7.0) containing 5 mM magnesium chloride, 6 mM UTP, 0.5% dextrin (W/V), and 1 unit/ml-substrate UDPG pyrophosphorylase, and the mixture was incubated at 30° C. to undergo reaction. The enzyme was inactivated by addition of 70% ethanol in an amount equivalent to the reaction amount. UDPG in the reaction mixture was determined by HPLC and the activity corresponding to formation of 1 μmol of UDPG at 30° C. for one minute is defined as one unit.

(3) Synthesis of UDPG Through Addition of UDPG Pyrophosphorylase, Maltdextrin Phosphorylase, and Dextrin to the UDPG-UTP Yeast Reaction Mixture To the UDPG-UTP solution (100 ml) prepared in (3) of Example 1, dextrin (Difco Co.) was added so that the final concentration thereof became 2% (W/V), and samples of UDPG glucose pyrophosphorylase and maltdextrin phosphorylase were added so that the respective concentrations thereof became 0.5 units/ml. The mixture was allowed to react at 30° C. for 30 hours. When the reaction mixture was subjected to HPLC analysis, a yield of 31.0 mM UDPG was confirmed.

Example 4

Synthesis of GDP-mannose (1) Cloning of a Gene of *Escherichia coli* GDP-mannose Pyrophosphorylase Chromosomal DNA of *Escherichia coli* ATCC 4157 was prepared by the method of Saito and Miura (Biochim. Biophys. Acta., 72, 619 (1963)). By use of the obtained DNA as a template, the following two primer DNAs were synthesized in accordance with a customary method. The *Escherichia coli* GDP-mannose pyrophosphorylase (manC) gene (Gordon Stevenson et al., J. Bacteriol., 178, 4885 (1996)) was amplified by PCR.

Primer (E): 5'-ATGCCGAATTCCCGTCGAAAC
TGA-3' (SEQ ID NO:5)

Primer (F): 5'-GGAATTCCGTTGGGGAAAT
TGCCG-3' (SEQ ID NO:6)

PCR amplification of the manC gene was performed by use of a DNA Thermal Cycler (Perkin-Elmer Cetus Instrument Co.) through 25 cycles of treatment, each cycle consisting of the steps of thermal denaturation (94° C., 1 minute), annealing (55 ° C., 2 minutes), and polymerization (72° C., 3 minutes), of a reaction mixture (100 µl) containing 50 mM potassium chloride, 10 mM Tris-hydrochloric acid (pH 8.3), 1.5 mM magnesium chloride, 0.001% gelatin, template DNA (0.1 µg), primer DNAs (E) and (F) (0.2 µM respectively), and AmpliTaq DNA polymerase (2.5 units).

After amplification of the gene, the reaction mixture was treated with a phenol/chloroform (1:1) mixture, and to an aqueous fraction was added ethanol in an amount twice the volume of the aqueous fraction to thereby precipitate DNA. The collected DNA precipitates were separated by agarose gel electrophoresis in accordance with the method of the literature ("Molecular Cloning," referred to above) to purify DNA fragments of 1.8 kb. The DNA was cleaved with restriction enzymes EcoRI and ligated with plasmid pUC18 (obtained from Takara Shuzo Co.) digested with the same restriction enzymes EcoRI using a T4 DNA ligase. The *Escherichia coil* K12 strain JM109 was transformed with the ligation mixture, and plasmid pUC18-manC was isolated from the obtained ampicillin-resistant transformant. The pUC18-manC is a product obtained by inserting into the EcoRI scission site downstream of the lac promoter, an EcoRI DNA fragment containing the *Escherichia coli* manC gene.

(2) Preparation of *Escherichia coli* GDP-mannose Pyrophosphorylase

*Escherichia coli* JM109 harboring plasmid pUC-manC was inoculated to a 2×YT culture medium (300 ml) containing 100 mg/l of ampicillin and was then subjected to shaking culture at 37° C. When the culture reached 4 ×10⁸ cells/ml, IPTG was added to the culture so that the final concentration thereof became 1 mM, and shaking culture was further carried out for five hours at 37° C.

After the cultivation, the cells were collected by centrifugation (9,000×g, 10 minutes) and then suspended in a buffer (60 ml) containing 50 mM Tris-hydrochloric acid (pH 7.5), 5 mM EDTA, 0.1% Triton X-100, and 0.2 mg/ml lysozyme. The suspension was maintained at 37° C. for one hour and then subjected to ultrasonic treatment so as to destroy the cells. The cellular residue was removed through additional centrifugation (20,000×g, 10 minutes). The thus-obtained supernatant fraction was provided as an enzyme sample. The GDP-mannose pyrophosphorylase activity of the enzyme sample and that of the reference bacterium (*Escherichia coil* JM109 harboring pUC18) are shown in Table 4 below.

TABLE 4

| Strain | GDP-mannose pyrophosphorylase activity (units/mg-protein) |
| --- | --- |
| JM109/pUC18 | <0.01 |
| JM109/pUC18-macC | 0.23 |

The unit GDP-mannose pyrophosphorylase activity was determined through measurement and calculation by use of the following method. An enzyme sample was added to 50 mM potassium phosphate buffer (pH 7.6) containing 1 mM magnesium chloride, 5 mM GTP, and 5 mM mannose-1-P, and the mixture was incubated at 37° C. to undergo reaction. The enzyme was deactivated by thermal treatment at 100° C. for five minutes. GDP-mannose in the reaction mixture was determined by HPLC, and the activity corresponding to formation of 1 µmol of GDP-mannose at 37° C. for one minute is defined as one unit.

(3) Preparation of a GDP-mannose-GTP Solution by Use of Dry Baker's Yeast

A reaction mixture (20 ml) of 40 mM GMP, 200 mM glucose, 200 mM potassium phosphate (pH 8.0), and 10 mM magnesium chloride was placed in a 100-ml beaker. Dry baker's yeast (2 g, Oriental Yeast Industries K. K.) was suspended in the reaction mixture. The mixture was allowed to react at 20° C. for seven hours with stirring. After completion of the reaction, the reaction mixture was treated at 100° C. for five minutes and the yeast cells were removed from the reaction mixture by centrifugation (2,000×g, 10 minutes). When the recovered supernatant was subjected to HPLC analysis, a yield of 11.2 mM GDP-mannose and 10.1 mM GTP was confirmed.

(4) Synthesis of GDP Mannose Through Addition of GDP-mannose Pyrophosphorylase and Mannose-1-P to the GDP-mannose-GTP Solution To the above-described GDP-mannose-GTP solution (200 µl) was added mannose-1-P so that the final concentration thereof became 20 mM, and GDP-mannose pyrophosphorylase was added so that the concentration thereof became 0.1 unit/ml. Water was added to the mixture so that the total volume became 400 µl, and the obtained mixture was allowed to react at 37° C. for eight hours. When the reaction mixture was subjected to HPLC analysis, a yield of 10.5 mM GDP-mannose was confirmed.

Example 5

The procedures of (3) and (4) of Example 4 were performed by addition of GDP-mannose pyrophosphorylase in an amount (as enzyme unit) of 0 unit, 0.025 units, 0.05 units, or 0.1 unit, to thereby obtain GDP-mannose.

Figure 2:
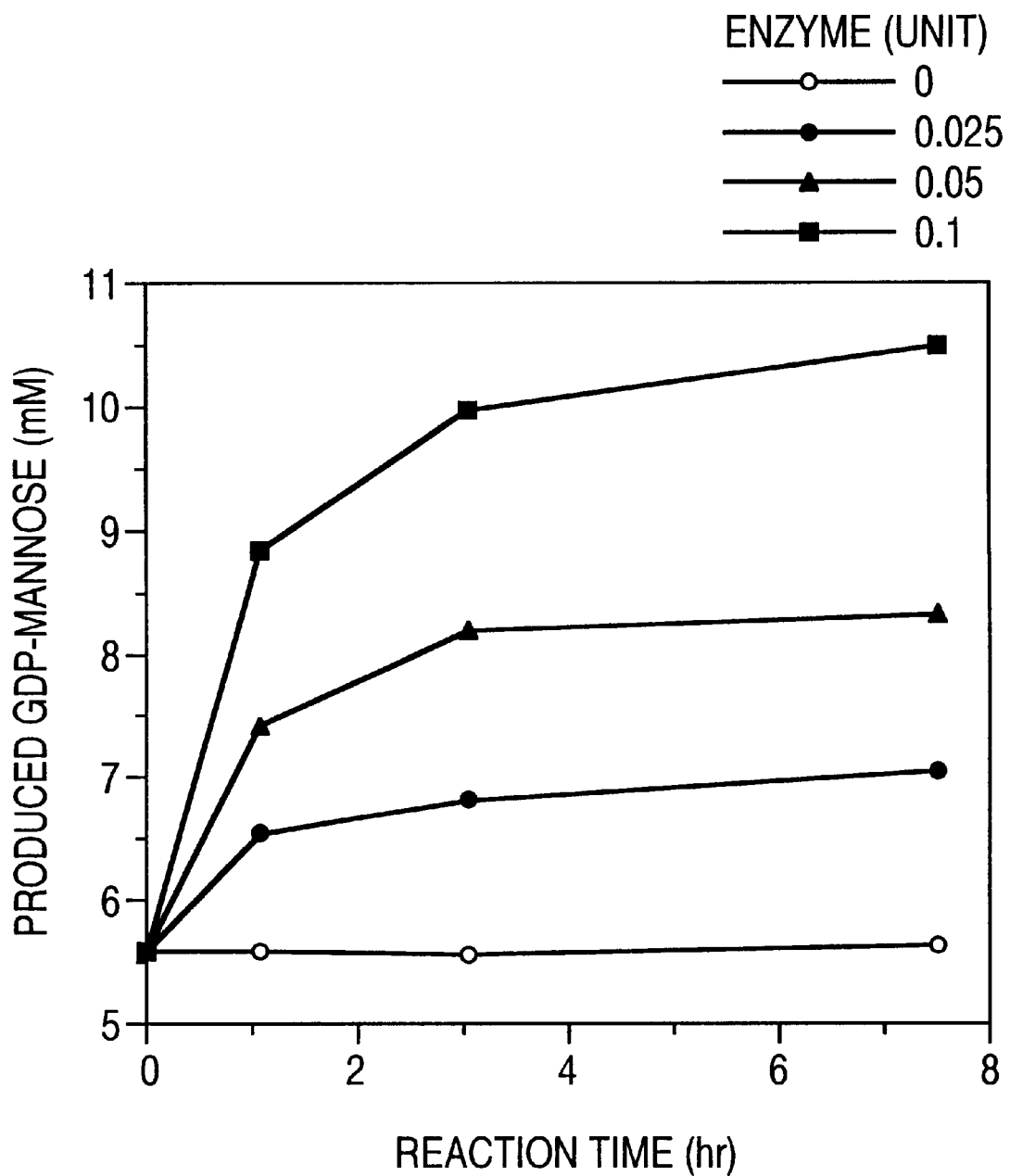
FIG. 2 shows chronological changes in the production yield of GDP-mannose.

Chronological changes in the amount of formation of GDP-mannose are shown in FIG. 2.

As shown above, the present invention enables the effective production of sugar nucleotides, which previously have been produced with low productivity through conventional yeast cell methods.

We claim:

1. A process for preparing uridine diphosphate-glucose (UDP-glucose), which comprises the steps of:
   adding yeast cells and uridine monophosphates (UMP) to a reaction system and reacting therewith to produce uridine triphosphates (UTP), and then
   deactivating the UTP synthesizing enzymes from the yeast cells when the production yield of UTP is maximized, and then
   adding UDP-glucose pyrophosphorylases and glucose 1-phosphates to the UTP-containing reaction system, to produce UDP-glucose.

2. A process for preparing UDP-glucose, which comprises the steps of:
   adding yeast cells and UMP to a reaction system and reacting therewith to produce UTP, and then
   deactivating the UTP synthesizing enzymes from the yeast cells when the production yield of UTP is maximized, and then adding UDP-glucose pyrophosphorylases and a glucose 1-phosphate production system which produces glucose 1-phosphates to the UTP-containing reaction system to produce the UDP-glucose.

3. The process according to claim 2, wherein the glucose 1-phosphate (G-1-P) production system includes phosphorylase.

4. The process according to claim 2, wherein the G-1-P production system produces G-1-P by reacting (1) saccharose with saccharose phosphorylase, (2) glycogen with glycogen phosphorylase, or (3) dextrin with maltdextrin phosphorylase.

5. The process according to claim 1, wherein a saccharide or an organic acid is added along with the yeast cells and the UMP to the reaction system.

6. The process according to claim 5, wherein the saccharide is glucose, fructose or sucrose.

7. The process according to claim 5, wherein the organic acid is acetic acid or citric acid.

8. The process according to claim 2, wherein a saccharide or an organic acid is added along with the yeast cells and the UMP to the reaction system.

9. The process according to claim 8, wherein the saccharide is glucose, fructose or sucrose.

10. The process according to claim 8, wherein the organic acid is acetic acid or citric acid.

11. The process according to claim 1, wherein an inorganic phosphoric acid is added along with the yeast cells and the UMP to the reaction system.

12. The process according to claim 11, wherein the inorganic phosphoric acid includes phosphate.

13. The process according to claim 12, wherein the phosphate is potassium phosphate.

14. The process according to claim 12, wherein the phosphate is in the form of a phosphate buffer.

15. The process according to claim 2, wherein an inorganic phosphoric acid is added along with the yeast cells and the UMP to the reaction system.

16. The process according to claim 15, wherein the inorganic phosphoric acid includes phosphate.

17. The process according to claim 15, wherein the phosphate is potassium phosphate.

18. The process according to claim 15, wherein the phosphate is in the form of a phosphate buffer.

* * * * *